United States Patent
Eckelt

(10) Patent No.: US 10,485,756 B2
(45) Date of Patent: Nov. 26, 2019

(54) RHEOLOGICAL BLOOD REPLACEMENT SOLUTION AND USES THEREOF

(71) Applicant: Universitätsmedizin der Johannes Gutenberg-Universität Mainz, Mainz (DE)

(72) Inventor: John Eckelt, Nackheim (DE)

(73) Assignee: Universitätsmedizin der Johannes Gutenberg-Universität Mainz, Mainz (DE)

( * ) Notice: Subject to any disclaimer, the term of this patent is extended or adjusted under 35 U.S.C. 154(b) by 0 days.

(21) Appl. No.: 15/559,631

(22) PCT Filed: Mar. 21, 2016

(86) PCT No.: PCT/EP2016/056141
§ 371 (c)(1),
(2) Date: Sep. 19, 2017

(87) PCT Pub. No.: WO2016/150909
PCT Pub. Date: Sep. 29, 2016

(65) Prior Publication Data
US 2018/0055763 A1    Mar. 1, 2018

(30) Foreign Application Priority Data

Mar. 25, 2015 (EP) .................................. 15160756

(51) Int. Cl.
| | |
|---|---|
| *A61K 9/00* | (2006.01) |
| *A61K 47/10* | (2017.01) |
| *A61K 47/38* | (2006.01) |
| *A61K 47/02* | (2006.01) |
| *G01N 33/96* | (2006.01) |

(52) U.S. Cl.
CPC ............ *A61K 9/0026* (2013.01); *A61K 47/02* (2013.01); *A61K 47/10* (2013.01); *A61K 47/38* (2013.01); *G01N 33/96* (2013.01)

(58) Field of Classification Search
CPC ....... A61K 9/0026; A61K 47/02; A61K 47/10
See application file for complete search history.

(56) References Cited

U.S. PATENT DOCUMENTS

| 4,001,401 A * | 1/1977 | Bonsen ................. C07K 14/805 514/13.4 |
| 7,696,176 B1 | 4/2010 | Norberg |
| 2007/0207962 A1 | 9/2007 | Coleman |

FOREIGN PATENT DOCUMENTS

WO    WO 2006/031209 A1 *   3/2006 ............... A61K 9/70

OTHER PUBLICATIONS

Moyers-Gonzalez, M. et al, "A non-homogeneous constitutive model for human blood. Part I: model derivation and steady flow", J. Fluid Mech., vol. 617, pp. 327-354, (2008).
Thurston, G., "Viscoelasticity of human blood", Biophysical Journal, vol. 12, pp. 1205-1217, (1972).
Owens, R., "A new microstructure-based constitutive model for human blood", J. of Non-Newtonian Fluid Mechanics, vol. 140(1-3), pp. 57-70, (2006) Abstract.
Lessner, J. et al, "The viscoelastic properties of whole blood", Theoretical and Clinical Hemorheology, Springer-Verlag, Berlin, pp. 194-205, (1971) Abstract.
Yilmaz, F., "A critical review on blood flow in large arteries; relevance to blood rheology, viscosity models, and physiologic conditions", Korea-Australia Rheology Journal, vol. 20(4), pp. 197-211, (Dec. 2008).
Moyers-Gonzalez,M. et al, "A non-homogeneous constitutive model for human blood. Part III. Oscillatory flow", J. Fluid Mech., vol. 155, pp. 161-173, Apr. 2008).
Vlastos, G. et al, "The superimposition of steady on oscillatory shear and its effect on the viscoelasticity of human blood and a blood-like model fluid", Biorheology, vol. 34(1), pp. 19-36, (Jan.-Feb. 1997) Abstract.
Sousa, P. et al, "Extensional flow of blood analog solutions in microfluidic devices", Biomicrolluidics, vol. 5(014108), pp. 1-19, (2011).
Brookshier, K. et al, "Evaluation of transparent blood analogue fluids-aqueous Xanthan gum glycerin", Biorheology, vol. 30, pp. 107-116, (1993).
Fukada, E. et al, "Blood modeling using polystyrene microspheres", Biorheology, vol. 26(2), pp. 401-413, (Feb. 1989) Abstract.

* cited by examiner

*Primary Examiner* — Pancham Bakshi
(74) *Attorney, Agent, or Firm* — McHale & Slavin, P.A.

(57) ABSTRACT

The present invention relates to a polymer solution for use as a rheological blood substitute. The rheological blood replacement solution comprises in its basic composition a water-soluble cellulose polymer with a molecular weight of 100 kDa or greater, polyethylene oxide and a solvent. The rheological blood replacement solution of the invention can be used in a variety of applications, e.g. as blood substitute, calibration agent or reference agent. The blood replacement solution is based on a polymer solution, which can also be used as pharmaceutical composition, e.g. for the prevention or treatment of haemorrhage or shock-related disorders.

12 Claims, 1 Drawing Sheet

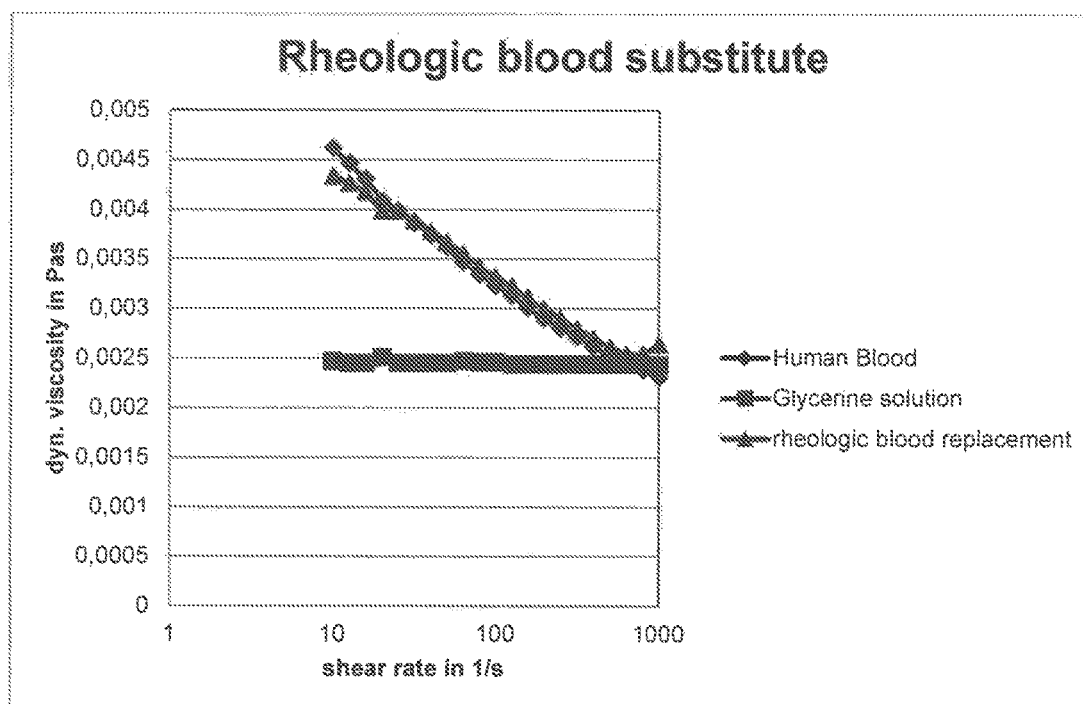

RHEOLOGICAL BLOOD REPLACEMENT SOLUTION AND USES THEREOF

CROSS REFERENCE TO RELATED APPLICATIONS

This is a national stage filing in accordance with 35 U.S.C. § 371 of PCT/EP2016/056141, filed Mar. 21, 2016, which claims the benefit of the priority of European Patent Application No. 15160756.1, filed Mar. 25, 2015, the contents of each are incorporated herein by reference.

FIELD OF THE INVENTION

The present invention relates to a polymer solution for use as a rheological blood substitute. The rheological blood replacement solution of the invention can be used in a variety of applications, e.g. as blood substitute, calibration agent or reference agent in clinical or analytical devices. The blood replacement solution is based on a polymer solution, which can also be used as pharmaceutical composition, e.g. for the prevention or treatment of haemorrhage or shock.

DESCRIPTION OF THE BACKGROUND ART

The human blood carries vital substances to cell tissues and organs of the body. Blood viscosity depends on blood composition, temperature, shear rate, vessel diameter, cell aggregation level, shape, deformation and plasma viscosity. Whole blood is a non-homogenous complex fluid, which exhibits very complex properties (R. G. Owens, J. Non-Newtonian Fluid Mech. 140, 57, 2006; M. Moyers-Gonzalez, R. G. Owens, and J. Fang, J. Fluid Mech. 617, 327, 2008). The circulatory system is a complex system of branching compliant tubes, which adjusts itself according to a number of control mechanisms. Because of this complexity, there is a number of variables which effect the functions, properties and responses of the circulatory system.

Early dynamic rheological measurements demonstrated a non-Newtonian behaviour of human blood (G. B. Thurston, Proceedings of the Sixth Conference of the European Society for Microcirculation, Aalborg (Karger, Basel, pp. 12-15, 1971; G. B. Thurston, Biophys. J. 12, 1205, 1972; A. Lessner et al., Theoretical and Clinical Hemorheology, Springer-Verlag, Berlin, pp. 194-205, 1971), whereas plasma can be considered as a Newtonian fluid (R. G. Owens, J. Non-Newtonian Fluid Mech. 140, 57, 2006; M. Moyers-Gonzalez, R. G. Owens, and J. Fang, J. Fluid Mech. 617, 327, 2008; M. Moyers-Gonzalez, R. G. Owens, and J. Fang, J. Non-Newtonian Fluid Mech. 155, 161, 2008; M. Moyers-Gonzalez, R. G. Owens, J. Non-Newtonian Fluid Mech. 155, 146, 2008). Non-Newtonian properties include viscoelasticity, thixotropy and shear-thinning behaviour. At low shear rates, red blood cells may form aggregates structures, causing an increased blood viscosity (G. B. Thorston and N. M. Henderson, Handbook of Hemorheology and Hemodynamcis, IOS, Amsterdam, pp. 72-90, 2007). In small vessels typical of the microcirculation system, e.g. arterioles and capillaries, where the characteristic times of the flow and the fluid become comparable, blood presents a viscoelastic behaviour (R. G. Owens, J. Non-Newtonian Fluid Mech. 140, 57, 2006).

A comprehensive characterization of blood rheology and its flow dynamics is indeed very important in order to predict cardiovascular diseases, to plan vascular surgeries, to understand the transport of drugs through the circulatory system, and for the development of cardiovascular equipment as, for example, blood pumps, heart valves and stants (F. Yilmaz and M. Y. Gundogdu. Korea-Aust. Rheol. J. 20, 197, 2008). However, the manipulation of whole blood is not a straightforward task and may not always be practical primarily due to safety reasons.

Blood analog solutions are widely used for in-vitro experiments as they exhibit several advantageous characteristics such as non-toxicity, low cost and transparency (G. B. Thorston, Advances in Hemodynamics and Hemorheology, JAI Press., Inc., Connecticut, Vol. I, pp. 1-30, 1996). A number of these fluids present rheological characteristics similar to human blood and are typically based on polymer solutions. One of the known solutions contains polystyrene spheres in a mixture of water, dextran 70 and calcium chloride to stimulate the aggregation process (E. Fukada, G. V. F. Seaman, D. Liepsch, M. Lee, and L. Friis-Baastad, Biorheology 26, 401, 1989). In addition, aqueous solutions of a polyacrylamide (PAA) and xanthan gum (XG) have been developed, in which the addition of glycerine was used to tune the blood rheology at different haematocrit levels (K. K. Brookshier and J. M. Tarbell, Biorheology 30, 107, 1993). It was found, however, that at high shear rates, the known blood analogs tend to exhibit higher viscosity and elasticity than whole blood (G. Vlastos, D. Lerche, B. Koch, O. Samba, and M. Pohl, Rheol. Acta 36, 160, 1997).

Since blood rheology is extremely complex, it is difficult to develop analog fluids that yield a complete description of all the rheological properties of blood. Typically, these fluids are chosen based on the density and shear viscosity. The known blood analog solutions described above suffer from the problem that the viscosity is essentially independent from the shear rate of the solution. Real blood exhibits a shear rate diminishing effect when viscosity increases.

The flow of blood analog solutions can be investigated in microchannels with dimensions comparable to small human vessels and flow visualisation techniques (P. C. Sousa et al., Extensional flow of blood analog solutions in microfluidic devices, Biomicrofluidics 5, 014108, 2011). The use of microchannels is advantageous because they are simplified representations of intensity stenoses typical of diseased microcirculatory vessels. Therefore, also possible medical conditions such as haemorrhage or shock can be addressed using blood substitute solutions. The rheology of blood analog fluids can be analysed by rotational rheometers or capillary brake-up extensional rheometers to determine the relaxation time of the fluid in extensional flow.

The studies known so far demonstrate that, at low flow rates, the known blood analog polymer solutions exhibit Newtonian-like flow patterns, i.e. an increase of the flow rate results in an appearance of symmetric vortices upstream of the contraction that increases in size with the flow rate due to the enhancement of elastic effects. When the flow rate is further increased, inertial effects also become important and symmetric vortices are observed downstream of the abrupt expansion similar to the Newtonian fluid flow.

There are also alternative solutions such as compositions comprising human serum albumin and amino acid solutions for use in treatment of hypovolemia or shock (U.S. Pat. No. 7,696,176 B1). A similar intravenous blood-replacement solution for rapidly restoring normal blood viscosity, rheology, osmolarity and hemodynamic stability has been described in U.S. 2007/0207962 A1. The solution comprises fibrinogen, albumin, fibronectin and an electrolyte.

SUMMARY OF THE INVENTION

In view of the above, the underlying problem of the present invention is to provide an improved polymer solution which better resembles the viscosity behaviour of human blood at different shear rates.

The solution provided is a rheological blood replacement solution as described in claim 1, a method of its manufacture, its uses and pharmaceutical compositions based thereon. Preferred embodiments are subject-matter of the dependent claims.

BRIEF DESCRIPTION OF THE DRAWING

FIG. 1 is a graph illustrating the behavior and properties of the rheological blood replacement solution with respect to viscosity and shear rate as compared with human blood and glycerine/water solution.

The rheological blood replacement solution is based on a polymer solution that comprises a water-soluble polymer with a molecular weight of 100 kDa or greater. Preferably, the water-soluble polymer is a cellulose or cellulose derivative having a high molecular weight and flexible chains. Depending on the embodiment, the water-soluble cellulose polymer is preferably selected from the group consisting of methyl cellulose, ethyl cellulose, propyl cellulose, and hydroxymethyl cellulose, hydroxyethyl cellulose, hydroxypropyl cellulose, hydroxybutyl cellulose, carboxy cellulose, carboxymethyl cellulose carboxyethyl cellulose, carboxybutyl cellulose, methylhydroxymethyl cellulose, ethylhydroxymethyl cellulose, propylhyroxymethyl cellulose, butylhydroxymethyl cellulose methylhydroxyethyl cellulose, ethylhydroxyethyl cellulose, propylhyroxyethyl cellulose, butylhydroxyethyl cellulose, cellulose nitrate, cellulose acetate, cellulose acetate phthalate, cellulose acetate succinate, cellulose acetate butyrate, methylcellulose phthalate, and ethylcellulose phthalate, and chemically modified forms thereof.

Modified cellulose comprises chemical compounds that are derived from cellulose. Cellulose derivatives include, but are not limited to methyl cellulose, sodium methyl cellulose, carboxymethyl cellulose, sodium carboxymethyl cellulose, methylhydroxyethyl cellulose, ethylhydroxyethyl cellulose, hydroxyethyl cellulose and hydroxypropyl cellulose.

The water-soluble cellulose polymer is blended with a polyethylene oxide in a suitable solvent. In an alternative embodiment, the solution therefore further contains silicone and/or polyvinyl pyrrolidone and/or polyvinyl alcohol and/or polyvinyl acetate and/or polyacrylic acid and/or polyacrylic acid ester and/or polymethacrylic acid ester and/or polyethylene and/or polyacrylamide.

The rheological blood replacement solution of the invention contains polyethylene oxide, which is required in order to fine tune the viscosity of the solution. For this purpose, polyethylene oxide with a low molecular weight (e.g. 200-10.000 g/mol) is preferred. Polyethylene oxide can also partly or fully substitute the water-soluble cellulose polymer in the solution when blended with components having high molecular weight (1-8 Mio g/mol).

The solvent that is used in the inventive rheological blood replacement solution is preferably demineralized water. The polymer solution of the invention resembles the rheological characteristics similar to human blood and overcomes the limitations of the polymer solutions provided by the state of the art such as aqueous solutions of polyacrylamide (PAA) and xanthan gum (XG). In these solutions, the addition of glycerine is used to tune the blood rheology at different haematocrit levels. However, as shown in the examples below, glycine-containing solutions have no viscosity-shear rate relationship that resembles that of human or animal blood.

The polymer solution of the invention has a similar viscosity-shear rate relation to human blood. It appears that the replacement of glycerine with polyethylene oxide is a major contribution in order to achieve these results. The polymer solution of the invention particularly overcomes the limitations of the known polymer solutions where the shear rate is independent from the actual viscosity of the fluid. Consequently, at low flow rates, the polymer solutions of the prior art rather show Newtonian-like flow patterns, whereas the rheological blood replacement solution of the invention shows flow patterns similar to human blood.

For certain applications the polymer solution of the invention further contains sodium chloride as ingredient. Preferably, sodium chloride is added at a concentration of between >0% and 0.9% per weight. The polymer solution contains 0.01% to 0.5% per weight of the water-soluble cellulose polymer and 0.01% to 5% per weight of the polyethylene oxide. The concentration of the polyethylene oxide depends on the molecular weight of the compound, which can be added either as polyethylene oxide with low molecular weight (i.e. 200-10.000 g/mol) or with high molecular weight (1-8 Mio g/mol). The rheology of the solution can be tested using conventional rheometers such as air bearing rheometers, rotational rheometers or extensional rheometers. Rheometric measurements allow for the determination of the relaxation time of the fluid in extensional flow.

The blood replacement solution of the invention reveals improved rheological properties to conventional polymer solutions and allows an application in a number of technical fields, where the use of blood analogs or blood replacement solutions is mandatory. For example, the rheological blood replacement solution of the invention can be used as a calibration agent in dialysis devices. The human dialysis blood is usually pumped through tubes, pipes or membranes that have different diameters. Often, glycerine-containing solutions are used in such dialysis apparatuses. In addition, the rheological blood replacement solution of the invention can be used as a reference agent in medical analysis devices, e.g. for the optical detection of blood cells that are pumped through capillaries with small diameters. The polymer solution of the invention allows a laminar flow and an alignment of the blood cell bodies. This behaviour results in a higher precision of the analysis values obtained with such medical devices.

Furthermore, the rheological blood replacement solution can be used as blood plasma expander for the treatment of a number of diseases such as sepsis with shock, haemorrhage, hemorrhagic shock, hypovolemic shock, burn injury, capillary leak syndrome, hypoalbuminemia, nephritic syndrome, or multi-organ failure. If patients suffer from high blood loss, usually a sodium chloride solution is applied that additionally contains hydroxyethyl sugar or dextrin. The sugar polymers used in these solutions are mainly used in order to adjust the viscosity at a pre-determined, constant value. The rheological properties of these solutions, however, are different to human or animal blood.

The polymer solution of the invention can also contain electrolytes such as sodium, potassium, magnesium and trace elements found in normal blood. As such the polymer solution of the invention is also suitable as pharmaceutical composition having a therapeutic or preventive effect on a human or animal body. For example, an intravenous blood substitute solution may also comprise fibrinogen, albumin, fibronectin and/or electrolytes.

The rheological blood replacement solution of the invention can therefore be used for the preparation of the medicament for the prevention and/or treatment of surgical stress syndrome, circulatory disorders, malignancies and for providing a blood substitute in an human or animal organism. The methods and treatments disclosed herein essentially apply to methods and compositions that stabilize the turbulence of an organism's blood in order to treat stress-related diseases.

The invention also concerns a pharmaceutical composition, comprising a rheological blood replacement solution as described herein. The pharmaceutical composition of the invention is suitable for use in the treatment and/or prevention of a human or animal medical disorder such as sepsis with shock, haemorrhage, hemorrhagic shock, hypovolemic shock, burn injury, capillary leak syndrome, hypoalbuminemia, nephritic syndrome, or multi-organ failure.

The present invention also concerns a method for the preparation of a rheological blood replacement solution which resembles the fluid properties of human or animal blood. The method comprises the step of up-mixing a water-soluble polymer with a molecular weight of 100 kDa or greater with polyethylene oxide and a solvent. A preferred water-soluble polymer is a cellulose polymer or cellulose derivative with a molecular weight of 100 kDa or greater. Preferably, the polyethylene oxide has a molecular weight of 200-10.000 g/mol. In a preferred embodiment, the water-soluble cellulose polymer is ethylhydroxyethyl cellulose with a particle size of 98%<500 μm and a Brookfield viscosity at 20° C./1% solution of at least 350 mPa·s. The polyethylene oxide has preferably a molecular weight between 200 and 10.000 g/mol and the solvent is preferably water or a pharmaceutically acceptable solvent. In addition, the pharmaceutical composition may contain fibrinogen, albumin, fibronectin and electrolytes such as sodium, potassium, magnesium and their salts, and trace elements.

When used as blood substitute, the rheological blood replacement solution effectively restores normal blood viscosity, rheology, osmolarity, turbulence and hemodynamic stability.

One major advantage of the polymer solution of the invention stems from the fact that the polymer solution of the invention exhibits flow properties that are similar to the flow properties of the human or animal blood. In particular, the shear rate-dependent viscosity of the solution is similar to the viscosity behaviour of whole blood, regardless of the local flow properties (such as different diameters in arteries or capillary vessels). The known blood plasma expander of the prior art do not resemble this behaviour effectively.

The present invention is further explained in the following examples.

Preparation of the Rheological Blood Replacement Solution

Ethylhydroxyethyl cellulose: Bermocoll EHM 500, AkzoNobel, 0.01-0.5% per weight

Polyethylene oxide: PEO 1000 g/mol, Fluka, 0.01-2% per weight

Sodium chloride: >99.5%, Sigma Aldrich, Up to 0.9% per weight

Water: demineralized water (Millipore equipment).

The components were mixed in the desired composition and concentrations. The polymer solution was prepared by solving the ingredients over night at room temperature with gently mixing. The solution was then ready for use.

Methods

The analysis was performed by means of an air bearing rheometer equipped with a cylindric geometry:

Equipment: air bearing rheometer UDS 200 (Anton Paar GmbH, Graz)

Temperature control: TEK-180 in combination with a Viscotherm VT2 thermostat

Geometry: Z1 double-gap cylinder geometry (Anton Paar GmbH, Graz)

20 ml of the homogenous solution was poured into the measuring gap of the rheometer and the upper cylinder was lowered into the gap. The solution was allowed to thermostat at a temperature of 37° C. for 15 minutes. The following measuring procedure was applied:

Pre-shear at a shear rate of 10 1/s for 30 seconds;

Shear rate was increased logarithmically from 10 to 1.000 1/s, 10 data points per decade, duration of data point: 30 to 3 seconds (logarithmic).

Results

In FIG. 1, the polymer solution of the invention was compared with human blood and glycerine/water solution as reference. Glycerine-containing solutions are presently used in a number of clinical applications as blood substitute. The experiment of FIG. 1 shows that the solution of the present invention equally resembles the behaviour and properties of human blood in respect of viscosity and shear rate. With increasing shear rates, the viscosity is decreased in a similar manner as seen for human blood. By contrast, the viscosity of the reference glycerine-containing solution remains equal with increasing shear rates. With the reference solution the viscosity is independent from the shear rate, and the viscosity of the glycerine solution only equals the viscosity of human blood at one particular shear rate.

The rheological property of the polymer solution of the invention thus reflects the biological properties of human blood, which might be explained by the fact that the blood cell bodies adjust themselves in flows using the polymer solution of the invention similar to the adjustments that can be seen in human blood. If the shear rate decreases (e.g. due to changing diameters of the blood vessels or other influencing parameters), the viscosity naturally increases both for human blood and the rheological blood substitute of the invention but remains the same for the glycerine-containing solution.

This experiment clearly demonstrates that the polymer solution of the invention is suitable as a blood substitute as it reflects the rheological properties of human or animal blood. As the shear rate will change with different diameters of the flow channel (for example in blood capillaries, arterioles or blood vessels), the polymer solution of the invention allows a comparison of shear rates at different viscosities and hence different environmental conditions.

In summary, the rheological blood substitute solution of the invention stimulates the flow properties of blood in a greater shear rate range than known solutions of the prior art. Furthermore, the polymer solution of the invention can be used in a variety of non-clinical and clinical applications and is suitable for the treatment or prevention of stress-related disorders. Finally, the rheological blood replacement solution can be manufactured in accordance with GMP practice and fulfils the conditions for safety and storability.

The invention claimed is:

1. A rheological blood replacement solution for use as blood substitute, comprising
0.01% to 0.5% per weight of a water-soluble cellulose polymer with a molecular weight of 100 kDa or greater,
0.01% to 5% per weight of polyethylene oxide,
a solvent.

2. The blood replacement solution according to claim 1, wherein the water-soluble cellulose polymer is a cellulose derivative selected from the group consisting of methyl cellulose, ethyl cellulose, propyl cellulose, and hydroxymethyl cellulose, hydroxyethyl cellulose, hydroxypropyl cellulose, hydroxybutyl cellulose, carboxy cellulose, carboxymethyl cellulose carboxyethyl cellulose, carboxybutyl cellulose, methylhydroxymethyl cellulose, ethylhydroxymethyl cellulose, propylhyroxymethyl cellulose, butylhydroxymethyl cellulose methylhydroxyethyl cellulose, ethylhydroxyethyl cellulose, propylhyroxyethyl cellulose, butylhydroxyethyl cellulose, cellulose nitrate, cellulose acetate, cellulose acetate phthalate, cellulose acetate succinate, cellulose acetate butyrate, methylcellulose phthalate, and ethylcellulose phthalate, and chemically modified forms thereof.

3. The blood replacement solution according to claim 1, wherein the solution further contains water-soluble silicone and/or polyvinyl pyrrolidone, polyvinyl alcohol and/or polyvinyl acetate and/or polyacrylic acid and/or polyacrylic acid ester and/or polymethacrylic acid ester and/or water-soluble polyethylene and/or polyacrylamide.

4. The blood replacement solution according to claim 1, wherein the solvent is demineralized water.

5. The blood replacement solution according to claim 1, wherein the solution further contains sodium chloride.

6. The blood replacement solution according to claim 1, wherein the solution contains polyethylene oxide with a molecular mass between 100 g/mol and $9 \times 10^6$ g/mol.

7. A rheological blood replacement solution according to claim 1 for use as blood plasma extender in the treatment of patients suffering of sepsis with shock, haemorrhage, hemorrhagic shock, hypovolemic shock, burn injury, capillary leak syndrome, hypoalbuminemia, nephritic syndrome, or multi-organ failure.

8. A rheological blood replacement solution according to claim 1 for use as calibration agent in dialysis devices.

9. A rheological blood replacement solution according to claim 1 for use as reference agent in medical analysis devices.

10. A pharmaceutical composition, comprising a rheological blood replacement solution according to claim 1 for use as blood substitute.

11. The pharmaceutical composition of claim 10 for use in the treatment and/or prevention of sepsis with shock, haemorrhage, hemorrhagic shock, hypovolemic shock, burn injury, capillary leak syndrome, hypoalbuminemia, nephritic syndrome, or multi-organ failure.

12. A rheological blood replacement solution according to claim 1 for use as medicament.

* * * * *